United States Patent [19]

Solar

[11] Patent Number: 5,549,119
[45] Date of Patent: Aug. 27, 1996

[54] VIBRATING TIP CATHETER

[75] Inventor: Ronald J. Solar, San Diego, Calif.

[73] Assignee: Cordis Corporation, Miami Lakes, Fla.

[21] Appl. No.: 305,695

[22] Filed: Sep. 13, 1994

[51] Int. Cl.$^6$ .................................................. A61B 5/00
[52] U.S. Cl. ................................. 128/772; 604/22
[58] Field of Search ........................... 128/657, 658,
  128/772; 604/95, 264, 280–283

[56] References Cited

U.S. PATENT DOCUMENTS 4,323,071  4/1982  Simpson et al. ................... 128/343
5,243,997  9/1993  Uflacker et al. ................... 128/772
5,322,509  6/1994  Rickerd ............................. 128/658
5,389,073  2/1995  Imran ................................ 128/658

*Primary Examiner*—Max Hindenburg
*Attorney, Agent, or Firm*—Michael W. Montgomery

[57]  ABSTRACT

The present invention represents improved catheters and guidewires for use in medical applications designed to transverse tortuous anatomical pathways and/or cross lesions/stenoses within body cavities and/or blood vessels wherein the catheters and guidewires are provided with an integral vibration means which enhances the ability of said catheters and guidewires to effectively cross the said lesions or stenoses.

10 Claims, 3 Drawing Sheets

VIBRATING TIP CATHETER

FIELD OF THE INVENTION

The present invention relates to the field of mechanical devices which are useful in medical applications and in particular to catheters and guidewires which are designed to cross lesions/stenoses within body cavities and/or blood vessels. More particularly, the present invention pertains to an improvement in such catheters and guidewires whereby these devices are provided with a vibration means which enhances the ability of said catheters and guidewires to effectively cross the lesions or stenoses.

BACKGROUND OF THE INVENTION

Various prior art devices are known which allow a user to insert a catheter/guidewire means into a body cavity or blood vessel so as to allow the user to deliver an inflatable dilatation balloon, cutting device or other therapeutic means to the area of need. In carrying out such procedures, which may be generally described as either angioplasty or atherectomy, the object is generally to effect the opening of a stenotic segment of a blood vessel.

Angioplasty uses a dilatation balloon positioned in an artery to dilate the arterial lumen at the stenosis. A typical angioplasty dilatation catheter is disclosed in Simpson et al., U.S. Pat. No. 4,323,071, incorporated herein by reference. The angioplasty device of the Simpson et al. patent includes an inflatable dilatation balloon which is attached to the distal end of a hollow catheter. The proximal end of the catheter is attached to a fluid source, providing fluid communication between the fluid source and the balloon.

To treat an arterial stenosis the dilatation balloon is introduced into the artery in a deflated state and guided through the artery over a guidewire to a position adjacent the stenosis. Fluid from the fluid source is then infused into the balloon via the catheter to inflate the dilatation balloon, which in turn dilates the lumen of the artery. The dilatation balloon is then deflated and removed from the artery.

While effective for dilating an arterial lumen at a stenosis, a balloon dilatation catheter such as that of Simpson et al. does not remove plaque from the artery. Also, balloon dilatation devices are often not effective with calcified lesions, long, tortuous lesions, or lesions that cannot be crossed with a guidewire. To address the shortcomings of angioplasty, a procedure termed atherectomy has been developed wherein a mechanical device cuts and/or ablades arterial plaque.

A stenotic segment of a blood vessel, i.e., a stenosis, presents a narrowed and often tortuous path through which the guidewire must be advanced, and in some cases the stenotic segment of the blood vessel may be almost completely blocked, i.e., occluded, with atherosclerotic plaque. A particular problem associated with angioplasty and atherectomy procedures generally is in moving the guidewire through or across a stenosis so that an inflatable dilatation balloon or a cutting device can be positioned within or adjacent to the stenosis. Accordingly, there is a need in the treatment of an occluded or narrowed blood vessel for a guidewire that can be easily moved through the stenotic segment of the blood vessel.

Furthermore, it has been found that the major reason a catheter procedure fails in the clinical setting is a result of the inability of a guidewire or a guidewire and a catheter, to cross a tortuous or stenotic (narrowed) path. Clinicians rely on the ability of such guidewires to transmit axial force, that is, "pushability," and their ability to follow the contours of the anatomy, that is, "trackability," to position these devices at the desired location. Often, when resistance is met, the clinician will shake or manually vibrate the proximal section of the catheter or guidewire to attempt to advance the device further. Although this technique is sometimes successful, if often fails because the movements are gross, the frequency is too low, the amplitude of vibration is too large and the transmission of axial force is very poor.

Uflacker et al., U.S. Pat. No. 5,243,997, incorporated herein by reference, discloses a hand-held vibrating device for vibrating a guidewire used in angioplasty and atherectomy procedures. The vibrating device taught there permits the guidewire to be more easily passed through a stenotic segment of a blood vessel. The Uflacker et al. vibrating device includes a case, an electric motor mounted within the case, and a clamp member coupled to the electric motor for releasably securing and vibrating the guidewire. In use the guidewire is threaded through a blood vessel to the site of a stenosis. The guidewire can then be clamped to the vibrating device, which is selectively actuated and manipulated to vibrate and push the guidewire through the stenosis.

While the device taught in the aforementioned U.S. Pat. No. 5,243,997 does provide some means for improving the mobility of a guidewire through a stenosis, nevertheless the remoteness of the vibrating means from the distal end of the guidewire which would come in contact with the stenosis, as well as the bulkiness of the vibrating means provided and the fact that it is not integral to the guidewire or catheter all present obvious limitations and serve to reduce the overall effectiveness of the vibrating means provided there. Moreover, such a construction would not be expected to be effective with catheters due to the length of catheters and the fact that the catheter material would dampen any vibratory motion.

OBJECTS OF THE INVENTION

It is an object of the present invention to provide an improved vibrating device for vibrating a catheter or guidewire such that the catheter or guidewire can be more easily moved through a stenotic segment of a blood vessel.

It is another object of the present invention to provide a vibrating device that is especially adapted for use in angioplasty and atherectomy medical procedures.

It is a further object of the present invention to provide a vibrating device for a catheter or guidewire that is integral to the catheter or guidewire, is easy to use and is also cost effective.

These and other objects of the invention will become more apparent in the discussion below.

SUMMARY OF THE INVENTION

The present invention provides for improved catheters and guidewires for use in medical applications designed to cross lesions within body cavities and/or blood vessels wherein the catheters and guidewires are provided with an integral vibration means which enhances the ability of said catheters and guidewires to effectively cross the said lesions or stenoses.

More particularly, the present invention provides for an microvibrating motor which is integral with the catheter or guidewire and which serves to impart vibrations to the distal end of said catheter or guidewire and/or to other points along the length of the catheter or guidewire as may be deemed appropriate for the particular procedure for which the said catheter or guidewire may be used. Additionally, the present invention provides for an electronic control means exterior to the catheter or guidewire which control means allows the user to vary the frequency, amplitude and direction of vibration.

The construction and obvious advantages of the improved catheters and guidewires provided for in the present invention will be more clearly understood from the following description of various specific embodiments when read in conjunction with the accompanying drawings.

DETAILED DESCRIPTION OF THE INVENTION

The present invention provides a means to improve the ability of catheters and guidewires to cross lesions/stenoses within body cavities and/or blood vessels, and to do so in a manner which is less traumatic The basic concept is to construct catheters and guidewires with an integral vibration means, preferably near the distal segments of the respective catheters and guidewires, to gently vibrate the catheter tip and/or guidewire tip across the stenotic segment. Vibration is turned on and off by a control means at the proximal end of the device. The amplitude and frequency of vibration, as well as direction of vibration, are adjustable.

By providing a vibration means at or close to the distal end of the catheter or guidewire, the force is transmitted in the most efficient manner and, by using an electronically micro-miniature controlled vibration means such as, for example, a vibratory micro-miniature motor, the amplitude, frequency and direction of vibration may be modified by the user to meet parameters which are optimal for traversing anatomical variations and/or stenotic segments. For example, the frequency of vibration could be from about 60 hz to about 20,000 hz, or even as high as ultrasonic. Moreover, a "gentle" vibration, such as is provided by the integral vibration means of the present invention, is much less traumatic to the anatomy of the patient than the gross manual shaking previously employed. Thus, the use of catheters and/or guidewires according to the present invention will result in fewer catheter/guide-wire-related complications and improved efficacy, for example, successful catheter placement, during interventional procedures.

The improvements of the present invention have application in any catheter-type device, and are not limited to a specific application. It is contemplated that one specific catheter technique that will greatly benefit from the present invention is balloon angioplasty and atherectomy.

Figure 1:
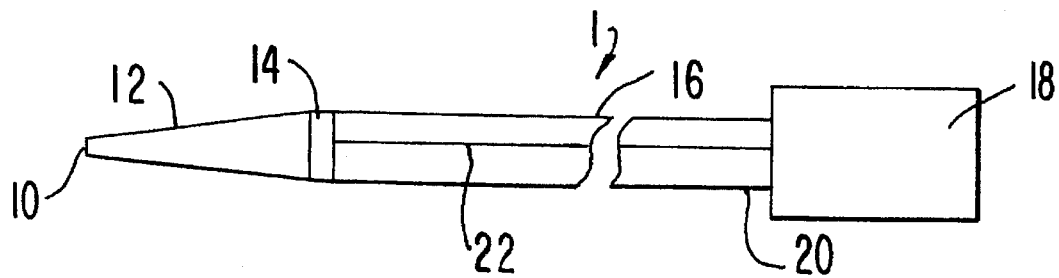
FIG. 1 is a schematic representation of a vibrating tip catheter according to the present invention.

The invention can perhaps be better understood by reference to the drawings. In FIG. 1 a preferred embodiment of the present invention is shown, where the balloonless catheter 1 comprises a distal end 10, a catheter tip 12, a vibrating means 14, a catheter shaft 16, an exterior control means 18 located at the proximal end 20 of the catheter shaft 16. Connecting the control means 18 and the vibrating means 14 is an electrical conduction means 22 to allow for transmission of the necessary control signals from the control means 18 to the vibrating means 14. Optionally, a wireless system could be used, or control means 18 could be positioned separate from the proximal end of catheter 2.

Figure 2:
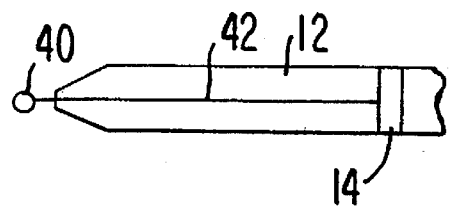
FIGS. 2 and 3 are schematic representations of distal sections of alternative embodiments of the vibrating tip catheter according to the present invention showing the location of the vibrating means in a balled tip, for both balloon and balloonless versions of said catheter.
Figure 3:
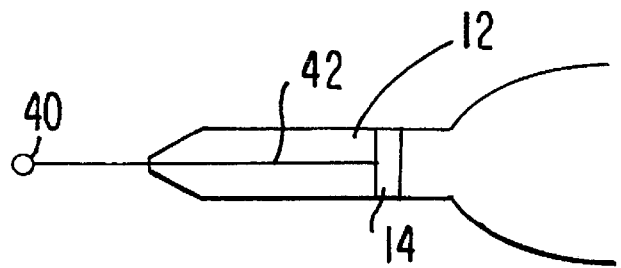

FIG. 2 represents an alternative embodiment for a non-dilatation balloon catheter according to the present invention employing a balled tip 40 which is directly connected via a shaft 42 to the vibration means 14 through the catheter tip 12. With reference to FIG. 3 another alternative embodiment for a balloon dilatation catheter according to the present invention similar to that of FIG. 2 is depicted also having a balled tip 40 which is directly connected via a shaft 42 to the vibration means 14 through the catheter tip 12.

Figure 4:
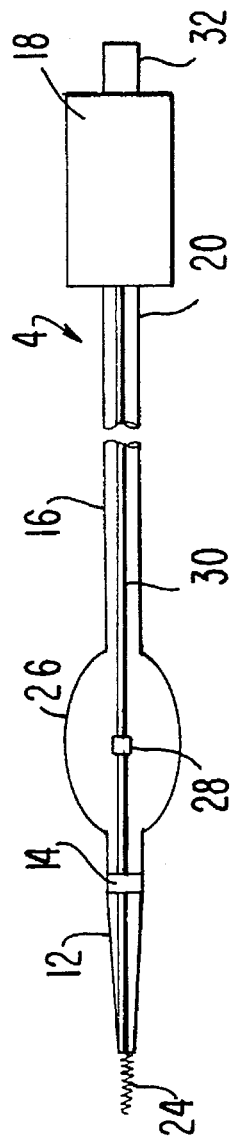
FIG. 4 is a schematic representation of a fixed wire vibrating tip balloon catheter according to the present invention.

With reference to FIG. 4, a fixed wire vibrating tip balloon dilatation catheter 4 according to the present invention is shown comprising a floppy guidewire spring tip 24 at the distal end of the catheter tip 12, a vibrating means 14, a balloon section 26, a catheter shaft 16, a radiopaque marker 28 located along the conductor/steering wire 30, said conductor/steering wire connecting the control means 18 electrically with the vibrating means 14 and physically with the guidewire tip 24. The catheter is also provided with an inflation port 32 in control means 18. The control means 18 and inflation port 32 are located at the proximal end 20 of the catheter shaft. The vibrating means 14 can be positioned distal to, within, or proximal to balloon 26.

Figure 5:
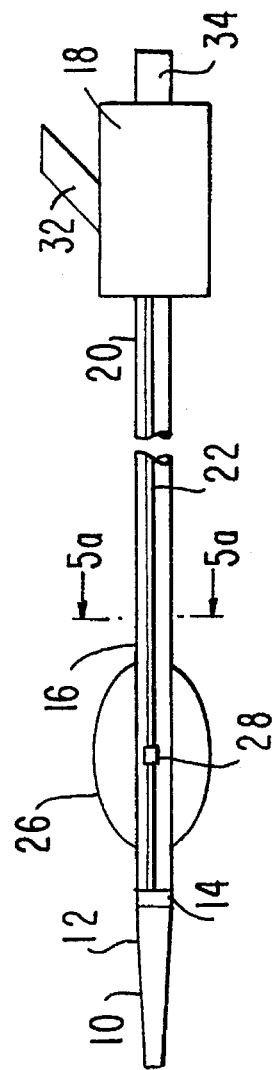
FIG. 5 is a schematic representation of an over-the-wire vibrating tip balloon catheter according to the present invention.

In reference to FIG. 5 an over-the-wire vibrating tip balloon dilatation catheter is shown comprising a distal end 10, a catheter tip 12, a vibrating means 14, a balloon section 26, a radiopaque marker 28 located along the catheter shaft 16 and a control means 18. Said control means 18 and vibrating means 14 are electrically connected by a conductor means 22. The proximal end 20 of the catheter shaft 16 is also provided with an inflation port 32 and a through lumen port 34.

Figure 5A:
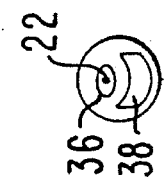
FIG. 5a is a cross-sectional view of the catheter shaft of FIG. 3 at the cross-section "A—A" showing one variation for the configuration of the inflation lumen and the through lumen.

With reference to FIG. 5a a cross-section of one embodiment of the catheter shaft of FIG. 5 taken at the section "5a—5a" is depicted showing the relative configuration of the inflation lumen 36 and the through lumen 38 in parallel arrangement. Alternatively, lumens 36 and 38 could be concentric, preferably with through lumen 38 within inflation lumen 36.

Figure 6:
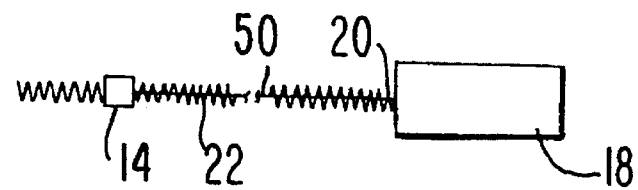
FIG. 6 is a schematic representation of a typical guidewire according to the present invention, showing the vibration means near the distal end.

In FIG. 6 a typical guidewire 50, having a vibration means 14, according to the present invention, is shown, wherein the guidewire is provided with an external control means 18, which is attached to the proximal end 20 thereof. The control means 18 is electronically connected to the vibrating means 14 by a conductor means 22. Optionally, a wireless system could be used, i.e., with no need for conductor means 22, or control means 18 could be positioned separate from the proximal end of guidewire 50.

Figure 7:
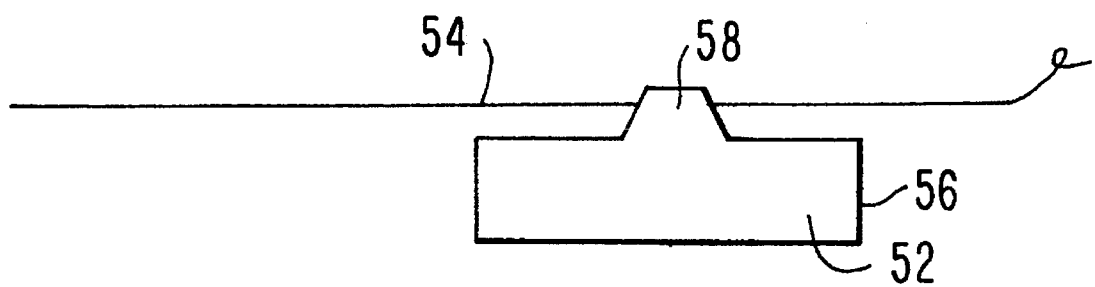
FIG. 7 is an oblique view of a representation of the invention wherein a vibratory means may be removably attached to the proximal end of a guidewire.

The vibration means incorporated into the catheters and guidewires of the present invention may also be located near the proximal end of the catheter or guidewire or at any other point or points along its length. Also, the vibration means and control means may be concentric to the catheter or guidewire, or they may be removable, such as is shown in FIG. 7, where a vibration means 52 is attached, preferably releasably or removably, to a guidewire 54, or to a catheter. The vibration means or device 52 for facilitating passage of a guidewire or catheter through, for example, a blood vessel, comprises a holding means, or more than one holding means, for releasably holding the guidewire or catheter and vibration means coupled to the holding means for vibrating the guidewire such that the guidewire or catheter may be held and advanced through the blood vessel. Moreover, vibration means 52 preferably comprises an integral control means so that an operator would manipulate controls on the exterior of case 56, such as an on-off switch or an exposed push button, to activate or de-activate a vibrator, such as an electric motor, having an external or, preferably internal battery, electrical source. Case 56 comprises, or is fixedly or slidably attached to, one or more guidewire clamp or attachment means 58, which transmit vibrations from the vibrator to the guidewire 54. Attachment means 58 can each be a clamp or other device that securely, preferably releasably or removably, attaches to guidewire 54. Optionally, one or more attachment means 58 could be fixedly attached to guidewire 54 with glue, solder, or the like. Further, each attachment means 58 may have a resilient member that contacts the guidewire 54.

Case 56 can comprise a hand held, in shape and size, vibrating means consisting of an electric vibrator motor, optionally where the output shaft or member of the electric motor is in contact with an attachment means 58, preferably so that the attachment means 58 moves back and forth in a single plane. Attachment means 58 may have a slot that reciprocates with and receives a stepped output shaft from the vibrator motor. The attachment means 58 may optionally be slidably attached to case 56 while in contact with the vibrator motor output shaft. For example, the attachment means may have a mounting slot that mates with a mounting track formed on case 56. Within case 56 a control circuit for operating the vibrator motor mounted within the case can be coupled to a power source and switch means for operating the motor. The power source could comprise a battery mounted to a printed circuit board, with an optional configuration for recharging the battery from an external power source. Also, case 56 may have internal structures, such as ribs, for forming separate compartments for attachment means 58, the vibrator motor, and/or a printed circuit board.

Generally, the catheters of the present invention may employ any type of therapeutic or diagnostic means, and be used in any type of therapeutic or diagnostic procedure. The shaft of the catheters of the present invention may be single lumen, multi-lumen, coaxial or other configuration, such as, for example, spring coil/helical coil or eccentric configurations. The catheters may be open ended or closed ended.

The vibration means used in the catheters and guidewires of the present invention may be placed anywhere along the catheter. However, a location close to the distal end of the catheter is generally preferred. Multiple locations, for example, from 2 to 4, along the length of the catheter shaft/guidewire are also contemplated by the present invention.

The conduction means, electrically connecting the vibrating means to the control means, may be a separate wire for conduction purposes, or an other catheter component, for example, a steering wire, core wire, spring body, as may be deemed appropriate in a particular catheter configuration. It is within the scope of the invention that the control means/vibrating means electrical connection may be wireless.

The control means may be simple on-off switch, or one which has the ability to vary the vibration parameters such as, amplitude, frequency and direction of vibration, using a variety of control functions as will be familiar to one skilled in this art.

The overall dimensions of the catheters of the present invention will vary. Typically the length of such catheters will be from about 5 cm–300 cm depending on application. For example, for intraoperative applications, 15 cm may be used, for PTA, 100 cm would be appropriate, and for PTCA, 140 cm or longer might be employed. The diameters would typically vary from about 0.5 mm to 4 mm, dependent upon application.

For applications where dilation of narrowings, such as stenoses or total obstructions, is required, it is contemplated that a catheter according to the present invention will not only cross the stenoses, but will dilate it to the diameter of the catheter. Catheter designs employing balloons may also incorporate the ability to do stepwise dilation. For example, the catheter might "vibrate" ("vibratory dilation") to the diameter of the vibration means, up to 2 mm for example, and then advance the balloon segment across stricture, blow up the balloon and dilate to larger "final desired" diameter again using vibratory dilation.

Preferably, guidewires according to the present invention will have the vibration means near their distal ends. Such guidewires may have a solid shaft, a hollow tube, spring coil or other configurations.

In addition to the use described above, the integral vibrating means employed in the present invention may also be applied to the additional applications listed below:

1. Atherectomy (directional, rotational, etc.)—the integral vibration means of the present invention will allow the device to cross tight strictures without predilation as is usually the case.
2. Amnioscopy, intravascular ultrasonography, endoscopy—again to allow placement in tight strictures.
3. Insertion of percutaneous introducer sheaths through sclerotic (scarred) tissue.
4. Placement of endovascular prostheses, such as intravascular stents.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A catheter for use in medical applications to cross lesions or stenoses within body cavities or blood vessels wherein the catheter is provided with at least one vibration means to enhance the ability of said catheter to effectively cross the lesions or stenoses, wherein one of said vibration means is located at or near the distal end of the catheter.

2. A catheter according to claim 1, wherein at least one vibration means is an integral micro-miniature vibratory motor.

3. A catheter according to claim 1, wherein at least one vibration means is controllable via an exterior electronic control means which permits a user to vary the amplitude, frequency and direction of vibration of the integral vibration means.

4. A catheter according to claim 1, wherein a plurality of vibration means are located at more than one point along the length of the catheter.

5. A catheter for use in medical applications to cross lesions or stenoses within body cavities or blood vessels wherein the catheter is provided with at least one vibration means to enhance the ability of said catheter to effectively cross the lesions or stenoses, said catheter having one of said vibration means located at or near the distal end of the catheter, a control means located exterior to the proximal end of the catheter, and a conductor means for transmitting control signals from the catheter means to said vibration means.

6. A guidewire for use in medical applications to cross lesions or stenoses within body cavities or blood vessels wherein the guidewire is provided with at least one vibration means to enhance the ability of said guidewire to effectively cross the lesions or stenosis, wherein one of said vibration means is located at or near the distal end of the guidewire.

7. A guidewire according to claim 6, wherein at least one vibration means is an integral micro-miniature vibratory motor.

8. A guidewire according to claim 6, wherein at least one vibration means is controllable via an exterior electronic control means which permits a user to vary the amplitude, frequency and direction of vibration of the integral vibration means.

9. A guidewire according to claim 6, wherein a plurality of vibration means are located at more that one point along the length of the guidewire.

10. A guidewire for use in medical applications to cross lesions or stenoses in body cavities or blood vessels wherein the guidewire is provided with at least one vibration means to enhance the ability of said guidewire to effectively cross the lesions or stenoses, said guidewire having one of said vibration means located at or near the distal end of the guidewire, a control means located exterior to the proximal end of the guidewire and a conductor means for transmitting control signals from the guidewire means to the vibration means.

* * * * *